United States Patent [19]

Serrero

[11] Patent Number: 5,723,115
[45] Date of Patent: Mar. 3, 1998

[54] INHIBITION OF ADIPOSE TISSUE DEVELOPMENT AND OBESITY

[75] Inventor: Ginette Serrero, Lake Placid, N.Y.

[73] Assignee: W. Alton Jones Cell Science Center, Inc., Lake Placid, N.Y.

[21] Appl. No.: 161,307

[22] Filed: Dec. 2, 1993

Related U.S. Application Data

[63] Continuation of Ser. No. 694,299, May 2, 1991, abandoned.
[51] Int. Cl.$^6$ .............. A61K 38/18; C07K 14/485; C07K 16/22
[52] U.S. Cl. ............ 424/85.1; 424/158.1; 530/399
[58] Field of Search ............ 530/399; 514/2, 514/909, 910; 424/85.8

[56] References Cited

U.S. PATENT DOCUMENTS

| | | | |
|---|---|---|---|
| 4,857,637 | 8/1989 | Hammonds et al. | 530/403 |
| 4,879,225 | 11/1989 | Morgan et al. | 435/68 |
| 5,084,396 | 1/1992 | Morgan et al. | 436/513 |

OTHER PUBLICATIONS

Serrero 1987 Biochem. Biophys. Res. Commun. 146:194.
Serrero & Mills 1987. J. Cell Biol 105(4 part 2): 274A.
Serrero & Mills. 1989 J. Cell. Biochem. Suppl. 0 (13pt E):242.
Hoath et al. 1986. Pediatric Res. 20(5):468–472.
Serrero & Mills. 1991 PNAS 88(9):3912.
Pettersson et al. 1984. Acta. Med. Scand. 215:447–451.
Adachi et al 1994 Endocrinology 135(4): 1824–1830.

*Primary Examiner*—Vasu S. Jagannathan
*Assistant Examiner*—Karen Cochrane Carlson
*Attorney, Agent, or Firm*—Browdy and Neimark

[57] ABSTRACT

Epidermal growth factor (EGF), which can act as a potent inhibitor of adipocyte differentiation in vitro, affects adipose tissue differentiation in vivo and can suppress obesity. Methods are provided for inhibiting the differentiation of adipocyte precursor cells, and for treating or preventing obesity, which comprise administering an effective amount of a composition capable of binding to and activating the EGF receptor, preferably epidermal EGF or a functional derivative thereof, TGFα, an antibody specific for the EGF receptor or an anti-idiotypic antibody specific for an idiotope on an antibody specific for EGF. Also provided is a method for determining the susceptibility of a subject to obesity or determining the presence of obesity associated with an abnormality in EGF or EGF receptor, which comprises measuring EGF in a body fluid or the amount or activity of EGF receptor protein or mRNA in adipocyte precursors.

11 Claims, 11 Drawing Sheets

CONTROL

EGF TREATED

INHIBITION OF ADIPOSE TISSUE DEVELOPMENT AND OBESITY

CROSS-REFERENCE TO RELATED APPLICATIONS

The present application is a continuation of application Ser. No. 07/694,299, filed May 2, 1991, now abandoned.

BACKGROUND OF THE INVENTION

1. Field of the Invention

The invention in the field of cell biology, physiology and medicine relates to methods for treating obesity and methods for determine susceptibility to obesity.

2. Description of the Background Art

Obesity has been declared a public health hazard by the National Institutes of Health. To combat this health problem, both prophylactic and therapeutic approaches are necessary. For prophylactic purposes, it would be useful to be able to predict and measure a person's propensity or susceptibility to obesity For therapeutic purposes, a means for interfering with the development or differentiation of adipocytes (fat cells) would be of great benefit. Furthermore, as a broader preventative approach to obesity, the ability to limit the fat content of food mammals would be of great importance. None of these desired objectives has been achieved. Early-onset obesity cannot be efficiently controlled by a weight reduction program once the obesity is apparent. Therefore, a means for early detection of early-onset obesity is imperative for its prevention.

The identification of the hormones controlling adipocyte proliferation and differentiation is very important for understanding normal adipose tissue development and for designing approaches for controlling abnormal states of adipose tissue development such as obesity. Several adipogenic cell lines able to undergo differentiation in vitro into fully mature adipocytes have served as model systems for investigating differentiation at the cellular and molecular levels (1–3). Using these cell lines, several hormones and growth factors have been shown to have adipogenic (3–5) or anti-adipogenic activities (6–9).

To determine whether a substance identified as influencing an adipogenic cell line is involved in the physiological regulation of adipose tissue development, one can investigate if adipocyte precursors in primary culture are responsive to this factor and ultimately if this factor can efficiently and specifically modulate adipose tissue development in vivo.

Epidermal growth factor (EGF) is a 6 kDa molecular weight polypeptide found in high concentrations in the submaxillary glands and at lower levels in the circulation (11–12). EGF affects the proliferation and the maintenance of functional properties of various mammalian cells in vitro (13–14). Animal experiments involving either injection of EGF, injection of antibodies specific for EGF, or removal of the major source of EGF by sialoadenectomy, have shown that EGF played a physiological role on the maintenance of several tissue functions in vivo (15–22). Recently, studies from the laboratory of the present inventor showed that EGF and transforming growth factor-α (TGFα) were potent inhibitor of the differentiation of primary culture adipocyte precursors isolated from inguinal fat pad of newborn rats (10).

Appropriate studies have not yet been performed which demonstrate that the effect of EGF on the function of adipose tissue occurs physiologically. It is to this activity, and its application in the control of obesity, that the present invention is directed.

SUMMARY OF THE INVENTION

An object of the present invention is to overcome the deficiencies described above.

The present inventor, through the performance of animal experiments, has discovered that epidermal growth factor (EGF), which can act as a potent inhibitor of adipocyte differentiation in vitro, affects neonatal adipose tissue development and obesity in vivo.

The present invention is thus directed to a method for inhibiting the differentiation of adipocyte precursor cells in a mammal, comprising administering to the mammal an effective amount of a composition capable of binding the epidermal growth factor receptor and stimulating the receptor.

Such a composition preferably comprises epidermal growth factor or a functional derivative thereof. Alternatively, the composition may comprise TGFα, an antibody specific for the epidermal growth factor receptor or an anti-idiotypic antibody specific for an idiotope on an antibody specific for epidermal growth factor.

The present invention is further directed to a method for preventing or treating obesity associated with a defect in epidermal growth factor quantity or activity in a mammal, comprising administering to the mammal an effective amount of a composition capable of binding the epidermal growth factor receptor and stimulating the receptor.

This obesity-treating or preventing composition preferably comprises epidermal growth factor or a functional derivative thereof. Alternatively, the composition may comprise TGFα, an antibody specific for the epidermal growth factor receptor or an anti-idiotypic antibody specific for an idiotope on an antibody specific for epidermal growth factor.

The present invention also provides a method for determining the susceptibility of a subject to obesity or determining the presence of obesity associated with an abnormality in epidermal growth factor level, which comprises obtaining a sample of a biological fluid from the subject and measuring the amount of epidermal growth factor in the fluid, the amount of the factor being inversely proportional to the susceptibility or the obesity.

In another embodiment, the invention provides a method for determining the susceptibility of a subject to obesity or the presence of obesity associated with an abnormality in epidermal growth factor receptor level or activity, which comprises obtaining a sample of adipose tissue from the subject and measuring the amount of epidermal growth factor receptor protein or mRNA in the tissue, or measuring the tyrosine kinase enzymatic activity of the receptor in the tissue, wherein the amount of receptor protein or mRNA or receptor activity is inversely proportional to the susceptibility or the obesity.

BRIEF DESCRIPTION OF THE DRAWINGS

FIG. 3A–3B is a graph showing the effect of increasing EGF doses on the number of adipocyte precursors and triglyceride content of inguinal fat pads. Values represent means±standard errors.

DESCRIPTION OF THE PREFERRED EMBODIMENTS

Figure 1A:
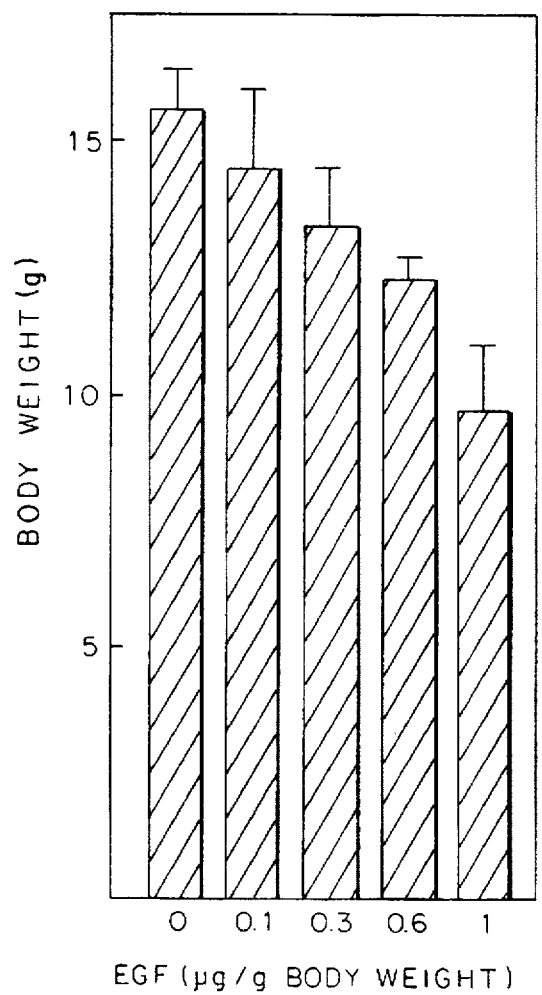
FIG. 1A–1B is a graph showing the effect of increasing EGF doses on body weight and fat pad weight of NBR rats. Each experiment included 6 to 8 newborn rats for each condition assayed. Results represent the mean (±standard error) of the values obtained from at least 3–5 separate experiments.

Based on the present inventor's discovery that EGF and TGFα inhibited adipocyte differentiation in vitro, the studies disclosed herein were performed demonstrating for the first time that EGF treatment in vivo has an inhibitory effect on adipocyte differentiation and promotes lower body weight.

Thus, according to the present invention, a subject, preferably a mammalian subject, more preferably a human, suffering from or being susceptible to obesity is treated with EGF or a functional derivative thereof. Such treatment may be performed in conjunction with other anti-obesity therapies, such as, for example, liposuction or lipectomy. Thus, after removal of adipose tissue, treatment with EGF or a functional derivative thereof will suppress further adipocyte differentiation, and thereby act to treat obesity.

A preferred composition for use according to the methods of the present invention comprises EGF or a functional derivative thereof (defined below). Also useful are other compounds which are capable of binding to and stimulating the EGF receptor, for example, TGFα (10) or an antibody specific for the EGF receptor or an anti-idiotypic antibody which mimics EGF.

Also useful for the methods of treating or preventing obesity according to the present invention are compounds which mimic the intracellular events which follow EGF receptor stimulation and thereby inhibit adipocyte differentiation. For example, EGF stimulates phospholipase A2 (PLA2, see Examples) in adipocytes, leading to activation of the cyclooxygenase pathway and the generation of arachidonic acid metabolites. Some of these metabolites, such as prostaglandin $F_{2\alpha}$ ($PGF_{2\alpha}$) can mimic the EGF effect on differentiation (see Examples). Therefore, according to the present invention, compounds which are generated following EGF receptor activation are used in the treatment or prevention of obesity.

Native purified or recombinant EGF molecule may be used in the methods of the present invention. Alternatively, functional derivatives of EGF may be used. By "functional derivative" is meant a "fragment," "variant," "analog," or "chemical derivative" of EGF, which terms are defined below. A functional derivative retains at least a portion of the function of EGF which permits its utility in accordance with the present invention.

A "fragment" of EGF refers to any subset of the EGF molecule, that is, a shorter peptide. A "variant" of EGF refers to a molecule substantially similar to either the entire EGF protein or a fragment thereof. Variant EGF peptides may be conveniently prepared by direct chemical synthesis using methods well-known in the art.

One variant comprehended by the present invention comprises a fusion protein between an active peptide of EGF capable of inhibiting adipocyte differentiation and a second amino acid sequence, for example an immunoglobulin chain constant region, which imparts stability to the molecule.

Also useful in the methods of the present invention is EGF or a functional derivative thereof linked to an antibody, preferably a monoclonal antibody, which is specific for a cell surface molecule characteristic of an adipocyte precursor. Such a complex would ensure more specific delivery of EGF to the appropriate target cell.

Amino acid sequence variants of EGF can be prepared by mutations in the DNA which encodes EGF. Such variants include, for example, deletions from, or insertions or substitutions of, residues within the amino acid sequence. Any combination of deletion, insertion, and substitution may also be made to arrive at the final construct, provided that the final construct possesses the desired biological activity. This biological activity can be tested by screening the variant for binding to the EGF receptor or inhibition of adipocyte differentiation in vitro.

Obviously, the mutations that will be made in the DNA encoding the variant EGF must not alter the reading frame and preferably will not create complementary regions that could produce secondary mRNA structure (see European Patent Publication No. EP 75,444).

The variants typically exhibit the same qualitative biological activity as the native EGF, specifically, the ability to bind to the EGF receptor and inhibit adipocyte differentiation.

Preparation of EGF variants in accordance herewith is preferably achievedby site-specific mutagenesis of DNA that encodes the native EGF protein or an earlier prepared variant. The technique of site-specific mutagenesis is well known in the art, as exemplified by Adelman et al., DNA 2:183 (1983). Typical vectors useful in site-directed mutagenesis include vectors such as the M13 phage, for example, as disclosed by Messing et al., *Third Cleveland Symposium on Macromolecules and Recombinant DNA*, Walton, A., ed., Elsevier, Amsterdam (1981). These phage are readily commercially available and their use is generally well known to those skilled in the art. For additional information related to site-directed mutagenesis, see Sambrook, J. et al. (*Molecular Cloning: A Laboratory Manual*, 2nd Edition, Cold Spring Harbor Press, Cold Spring Harbor, N.Y. (1989)).

Another group of variants are those in which at least one amino acid residue in the EGF sequence, and preferably, only one, has been removed and a different residue inserted in its place. Such substitutions preferably are made in accordance with the following list when it is desired to modulate finely the characteristics of a peptide molecule.

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional properties are made by selecting substitutions that are less conservative than those in the above list, that is, by selecting residues that differ more significantly in their effect o maintaining (a) the structure of the peptide backbone in the area of the substitution, for example, as a sheet or helical conformation, (b) the charge or hydrophobicity of the molecule at the target site, or (c) the bulk of the side chain. The substitutions that in general are expected to those in Rich (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the peptide molecule. However, when it is difficult to predict the exact effect of the substitution, deletion, or insertion in advance of doing so, one skilled in the art will appreciate that the effect will be evaluated by a routine screening assays, such as assaying direct binding of the EGF variant to the EGF receptor or competition of binding or labeled EGF.

An "analog" of EGF refers to a non-natural molecule substantially similar to either the entire molecule or a fragment thereof.

A "chemical derivative" of EGF contains additional chemical moieties not normally a part of the polypeptide. Covalent modifications are included within the scope of this invention. Such modifications may be introduced into the molecule by reacting targeted amino acid residues with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4- ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking EGF to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of EGF and the like. Moieties capable of mediating such effects are disclosed, for example, in *Remington's Pharmaceutical Sciences*, 16th ed., Mack Publishing Co., Easton, Pa. (1980).

Because adipocyte differentiation is inhibited through the action of EGF at its receptor, it is expected that stimulation of the EGF receptor of adipocytes by other agents capable of stimulating this receptor will result in similar effects. This can be accomplished using other reagents known in the art, for example, TGFα (10), antibodies specific for the EGF receptor, either polyclonal, monoclonal or chimeric. Additionally, anti-idiotypic antibodies specific for an idiotope on anti-EGF antibodies would be expected to have the capacity to mimic EGF action at its receptor. Such anti-idiotypic antibodies are also useful in the methods in which EGF and stimulatory antibodies to the EGF receptor are useful according to the present invention.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110; de St. Groth, S. F. et al., *J. Immunol. Methods*, 35:1–21 (1980); and Hartlow, E. et al., *Antibodies: A Laboratory Manual*, Cold Spring Harbor Laboratory Press, Cold Spring Harbor, N.Y., 1988). Such antibodies may be of any immunoglobulin class including IgG, IgM, IgE, IgA, IgD and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Hybridoma supernatants are screened for the presence of antibody specific for EGF receptor by any of a number of immunoassays, including dot blots and standard enzyme immunoassays (EIA or ELISA), which are well-known in the art. Once a supernatant has been identified as having antibodies, it may be further screened by Western blotting to verify the size of the antigen to which the antibody binds. One of skill in the art will know how to prepare and screen such hybridomas without undue experimentation in order to obtain a desired mAb.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Application 171496 (published Feb. 19, 1985); Robinson et al., International Patent Publication #PCT/US86/02269 (published 7 May 1987); Liu et al., *Proc. Natl. Acad. Sci. USA* 84:3439–3443 (1987); Better et al., *Science* 240: 1041–1043 (1988)). These references are hereby incorporated by reference.

An anti-idiotypic (anti-Id) antibody is an antibody which recognizes unique determinants (idiotopes) generally associated with the antigen-binding site of an antibody. See, generally: *Idiotypy in Biology and Medicine*, Academic Press, New York, 1984; *Immunological Reviews* Volume 79, 1984; *Curr. Top. Microbiol., Immunol.* Volume 119, 1985; *Immunological Reviews* Volume 90, 1986; which references are hereby incorporated by reference. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these determinants (the anti-Id antibody).

Accordingly, a mAb specific for EGF may be used to induce anti-Id antibodies in suitable animals, such as BALB/c mice. Spleen cells from such immunized mice are used to produce anti-Id hybridomas secreting anti-Id mAbs.

The term "antibody" as used herein is also meant to include intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)). Such fragments are typically produced by proteolytic cleavage, using enzymes such as papain (to produce Fab fragments) or pepsin (to produce F(ab')$_2$ fragments). It will be appreciated that Fab and F(ab∞)$_2$ and other fragments of the antibodies useful in the present invention may be used according to the methods disclosed herein for intact antibody molecules.

A typical regimen for preventing, suppressing, or treating obesity comprises administration of an effective amount of EGF or a functional derivative thereof, or a compound which stimulates the EGF receptor, administered over a period of several weeks, up to and including several months or even years.

It is understood that the dosage administered will be dependent upon the age, sex, health, and weight of the recipient, kind of concurrent treatment, if any, frequency of treatment, and the nature of the effect desired. The ranges of effective doses provided below are not intended to be limiting and represent preferred dose ranges. However, the most preferred dosage will be tailored to the individual subject, as is understood and determinable by one of skill in the art.

The total dose required for each treatment may be administered by multiple doses or in a single dose. The EGF protein or peptide derivative, or other compound which stimulates the EGF receptor, may be administered alone or in conjunction with other therapeutics directed to obesity.

Effective amounts of the EGF protein, functional derivative thereof, or compound stimulating the EGF receptor such as TGF$\alpha$ (10) an anti-receptor antibody or an EGF-mimicking anti-idiotypic antibody, are from about 0.01 µg to about 100 mg/kg body weight, and preferably from about 10 µg to about 50 mg/kg body weight.

Pharmaceutical compositions comprising the proteins, peptides or antibodies used according to the method of the invention include all compositions wherein the protein, peptide or antibody is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically.

For example, administration may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

Preparations for parenteral administration include sterile aqueous or non-aqueous solutions, suspensions, and emulsions, which may contain auxiliary agents or excipients which are known in the art. Pharmaceutical compositions for oral administration include tablets and capsules which can be prepared according to routine methods. Pharmaceutical compositions include suitable solutions for administration by injection or orally, and contain from about 0.01 to 99 percent, preferably from about 20 to 75 percent of active component (e.g., the EGF protein or functional derivative) together with the excipient.

In another embodiment of the present invention, in an individual genetically predisposed to obesity because of a deficiency in EGF, gene therapy can be used to insert into adipocytes DNA capable of expressing EGF. For example a cDNA construct encoding EGF can be linked to a fat-specific enhancer element, such as one described by S. R Ross et al. (*Proc. Natl. Acad. Sci. USA* 87:9590–9504 (1990)), resulting in EGF expressed in adipocytes. Alternatively, if the defect is related to an abnormal EGF receptor, a cDNA construct encoding the EGF receptor can similarly be linked to a fat-specific enhancer. An abnormal or dysfunctional EGF or EGF receptor is then replaced by infusion of the genetic construct in a form in which it can transfect cells of the appropriate lineage. Alternatively transfected cells of the desired lineage can be infused into the subject.

The present invention also provides a method for diagnosing a form of obesity associated with abnormal levels of EGF. In this method, a biological fluid, preferably plasma or serum is obtained and the amount of EGF present measured.

By the term "biological fluid" is intended any fluid derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term as used herein is a tissue extract, or the culture fluid in which any cells or tissue preparation from the subject has been incubated.

The measurement of EGF concentration may be made using any of a number of assays well-known in the art, such as immunoassays including radioimmunoassays (Chard, T., In: Work, T. S. et al., *Laboratory Techniques and Biochemistry in Molecular Biology*, North Holland Publishing Company, N.Y., (1978)) or enzyme immunoassays (Maggio, E. (ed.), *Enzyme Immunoassay*, CRC Press, Boca Raton, Fla., 1980). According to this method, a level of plasma EGF significantly below normal may be indicative of susceptibility to obesity, or the presence of obesity which is associated with EGF function.

In another embodiment of the present invention, the method for diagnosing a form of obesity associated with EGF function is based on an EGF receptor abnormality. In this method, adipocyte precursor cells are obtained from a subject in the form of a fat biopsy. EGF receptor level is measured either as binding of labeled, preferably radiolabeled, EGF in vitro or binding of an antibody specific for an EGF receptor, using standard methods. Alternatively, using nucleic acid hybridization techniques (Sambrook et al., supra), a labeled probe can be used to measure expression of the EGF receptor gene by quantitating the EGF receptor mRNA, using methods well-known in the art. Alternatively, EGF receptor activity can be assessed as post-binding receptor activity, such as by measuring receptor tyrosine kinase enzymatic activity, stimulation of cyclooxygenase, or generation of arachidonic acid metabolites (such as prostaglandin $F_{2\alpha}$). EGF receptor binding activity can also be accomplished in vivo by infusion of radiolabeled EGF or anti-EGF receptor antibody, followed by detection of binding in sites of interest by well-known radioimaging techniques (Sutton, *A Textbook of Radiology and Imaging*, 3rd Ed., Churchill Livingston, 1980; *Clinical Nuclear Medicine*, Maysey et al., ed., W. B. Sanders, 1983.). For in vivo diagnosis, radionuclides may be bound to EGF or a functional derivative thereof, or an anti-EGF receptor antibody, either directly or indirectly by using an intermediary functional group. Intermediary functional groups which are often used to bind radioisotopes which exist as metallic ions to chemotactic peptides are the chelating agents, diethylene triamine pentaacetic acid (DTPA) and ethylene diamine tetracetic acid (EDTA).

Having now generally described the invention, the same will be more readily understood through reference to the following examples which are provided by way of illustration, and are not intended to be limiting of the present invention, unless specified.

EXAMPLE I

Materials and Methods

Animals

New Zealand Brown (NBR) rats (Trudeau Institute, Saranac Lake, N.Y.) were mated in the animal facilities of the W. Alton Jones Cell Science Center. One day after delivery, litter size was adjusted to 6–8 pups/female according to the size and age of the females. No more than 8 pups/female were used. Mothers were fed ad libitum a regular laboratory diet and were allowed free access to water. Animals were housed in rooms in which the air flow, temperature and lights were controlled (12 h of light between 6 AM to 6 PM).

Treatment

Mouse "receptor grade" EGF (Biomedical Technologies, Inc.) was used in all experiments. This EGF was shown to have full biological activity as assessed by binding in a radioreceptor assay and by inhibition of adipose differentiation in primary cultures of adipocyte precursors (10). Beginning at 24 hrs after birth, rats were injected subcutaneously (sc) daily for 10 days with EGF dissolved in physiological saline at doses varying between 0.1 and 1.0 µg/g of body weight. The pups were weighed prior to each injection. Control animals were similarly handled and weighed, and were injected sc with an equivalent volume of physiological saline.

Primary Culture of Adipocyte Precursors of Inguinal Fat Pads

Inguinal fat pads, well developed in 10 day-old animals, can be easily dissected. Inguinal fat pads were excised, weighed and pooled. They were digested with collagenase using the method of Bjorntorp et al. (23), and duplicate aliquots were kept for measuring triglyceride content as described below. Digestion conditions minimized breakage of adipocytes during the incubation period (23). After digestion, the cell suspension was filtered through a 253 µm nylon mesh filter. Adipocytes were easily recovered by two successive flotations of the cell suspension. The infranatant containing the adipocyte precursors was removed with a plastic pipet and further filtered through an 80 µm nylon mesh. The adipocytes remained in the tube after removal of the infranatant. They were gently resuspended in culture medium and counted in a hemocytometer. The filtrate containing the adipocyte precursors was centrifuged twice at 200×g for 5 minutes. Adipocyte precursor pellets were resuspended in 4F medium. The cells were subsequently counted in a hemocytometer and inoculated in 35 mm dishes in 4F medium as described previously (24). Such cultures were used to evaluate the cells' ability to differentiate and to measure their responsiveness to EGF.

The defined medium designated 4F consists of a 1:1 mixture of Dulbecco's modified Eagle's medium (DME) and Ham's F12 medium (DME-F12 medium) containing 15 mM HEPES, pH 7.4, 1.2 mg/ml sodium bicarbonate, 50 µg/ml gentamicin, and the following mixture of proteins: fibronectin (2.5 µg/ml), insulin (10 µg/ml), transferrin (10 µg/ml) and fibroblast growth factor (10 ng/ml). The medium was originally developed to support the differentiation of the adipogenic cell line, 1246 (25). When cultivated in this medium, optimal differentiation of adipocyte precursors was achieved within 8 days of culture (24).

Measurement of Triglyceride Content in Inguinal Fat Pads

For determination of triglyceride content, lipids were extracted from duplicate aliquots of the fat pad cell suspensions obtained as above pads, using the method of Bligh et al. (26). Triglycerides were separated by thin-layer chromatography on silica gel plates using hexane/dimethyl ether/formic acid (60:40:1) as a solvent system. Spots containing triglycerides were scraped, and the triglyceride content was determined by the method of Marsh et al. (27). This method consists of a quantitative charring of the triglycerides at 200° C. for 15 min in the presence of concentrated sulfuric acid. Absorbance of the samples at 350 nm was measured in a spectrophotometer using known amounts of triolein as standards.

EXAMPLE II

Effect of EGF Injection on Fat pad Weight and Development

Ten separate in vivo experiments were performed with neonatal NBR rats. Over the 10 day period, pups injected with saline alone or with EGF were weighed daily. The efficiency of EGF injected was assessed by monitoring the "eyelid response," by determining the postnatal day on which eyelid opening occurs, which is related to the EGF dose (28). Eyelid opening occurred at day 8 in rats injected with EGF at a concentration of 1 µg/g body weight, 24 hrs later in rats treated with 0.6 µg EGF/g body weight, and 48 hrs later in rats injected with 0.3 µg EGF/g body weight. When the experiment was terminated, at day 10, eyelid opening had not yet occurred in rats injected with 0.1 µg EGF/g body weight and in control animals.

In addition to a change in eyelid opening, acceleration of incisor eruption and delay in hair growth were also observed in EGF-treated animals compared to control animals, as was described previously (13).

Body weight was significantly lower in animals that received EGF than in saline controls (FIG. 1, left panel). The decrease in weight gain observed in the EGF-treated animals varied with the dose of EGF (FIG. 1A). In animals injected with 1 µg EGF/g body weight, the weight was 40% less than in control animals. The observed EGF-associated decrease in weight agrees with the results of Hoath (17) and Heimberg et al. (29).

Figure 1B:
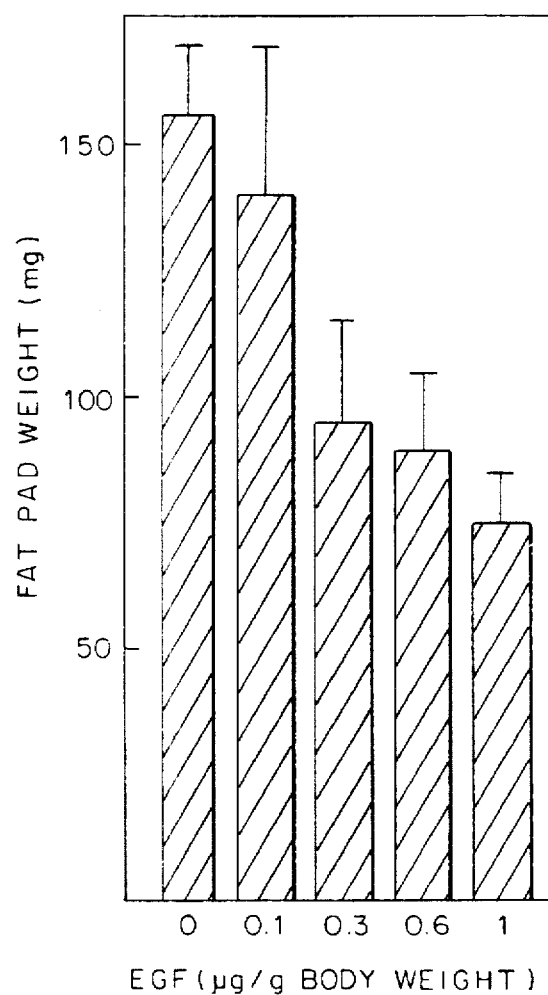

At the end of the experiment, all animals were sacrificed to determine inguinal fat pad weight. The inguinal fat pad is a well developed fat pad in newborn animals and its state of development is unrelated to sex. The average fat pad weight was lower in EGF-treated animals than in controls (FIG. 1B). In animals injected with 1 µg of EGF/g body weight, the inguinal fat pad weight was 50% lower than in controls (FIG. 1A). Although some decrease in kidney weight was observed, liver weight was unchanged whereas intestinal weight was increased by EGF treatment. These findings indicate that the effect on fat pad was not due to a generalized inhibitory action of EGF newborn rat development.

Figure 2A:
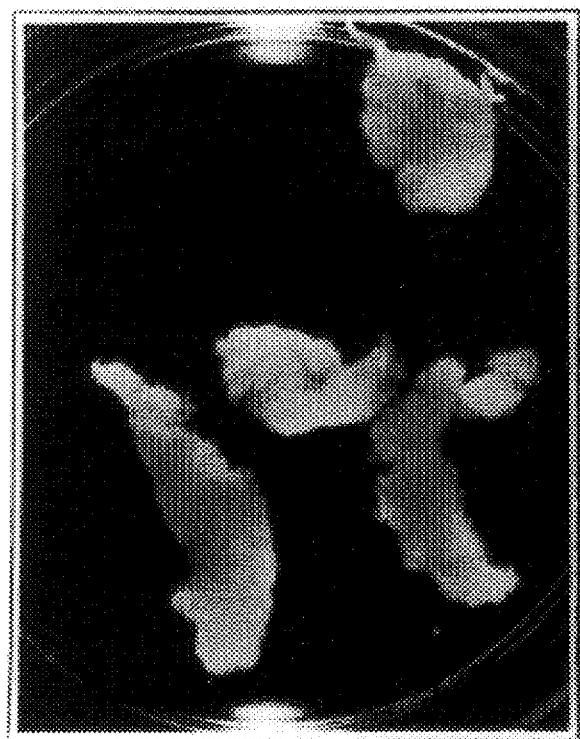
Figure 2B:

The change in inguinal fat pad weight induced by EGF treatment was accompanied by a difference in fat pad size and morphology (FIG. 2A-2B).

Figure 3A:
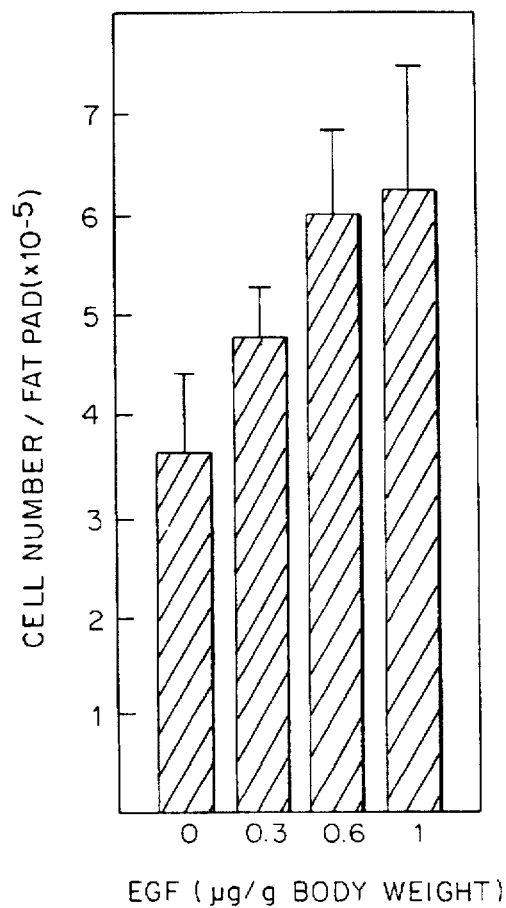
FIG. 3A–3B is a photograph of inguinal fat pads from normal animals (left panel) and from animals injected for 10 days with EGF at a concentration of 1 µg/g body weight (right panel).

After excision, inguinal fat pads were digested with collagenase to separate adipocyte precursors from mature adipocytes (23). The number of adipocyte precursors from duplicate samples was counted with a hemocytometer. It was found that the number of adipocyte precursors per fat pad was higher in inguinal fat pads from EGF-treated animals compared to controls (FIG. 3A). In EGF-treated animals (1 µg/g body weight), the number of adipocytes precursors was 1.8-fold higher than in control animals.

Figure 3B:
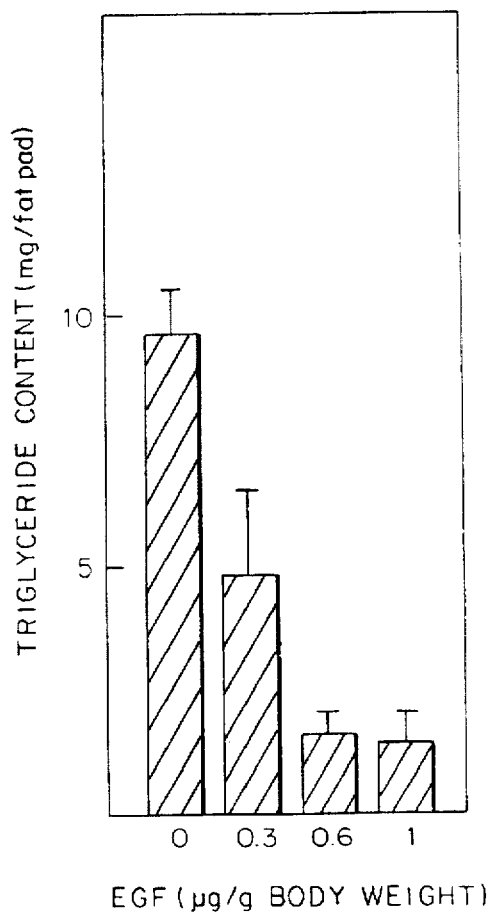

As a marker for the differentiation that occurred in the fat pads in vivo, the fat pad triglyceride content was determined. The amount triglyceride content was significantly lower in EGF-treated animals (FIG. 3B). It was 80% lower for fat pads isolated from animals treated with 1 µg EGF/g body weight (FIG. 3B). This decrease in triglyceride accumulation in fat pads of EGF-treated animals was correlated with a decrease in the number of mature adipocytes. In animals treated with 1 µg EGF/g body weight, the number of mature adipocytes in the fat pad was 4-fold lower than in control animals. However, the total number of cells (precursors plus adipocytes) was 40% lower in the fat pads of EGF-treated animals compared to controls. These results suggest that the increased number of adipocyte precursors in EGF-treated animals was not caused by a stimulation of total cell proliferation. Rather, it is thought that EGF delayed differentiation, leading to a smaller number of precursors undergoing differentiation and entering into the pool of triglyceride-laden adipocytes during the duration of the experiment.

EXAMPLE III

Comparison of Differentiation Capacity of Isolated Adipocyte Precursors

It was shown previously (24) that adipocyte precursors freshly isolated from inguinal fat pads of 48 hr-old rats proliferated and differentiated in 4F medium (see above). Adipocyte precursors isolated from inguinal fat pads of control and EGF-treated rats were cultivated in 4F medium to determine if their differentiation capacity had been affected by prior EGF treatment in vivo.

To monitor proliferation and differentiation, cells were harvested at day 8, the time of optimal differentiation of controls cells. Differentiation was followed by measuring the specific activity of the enzyme, glycerol-3-phosphate dehydrogenase (G3PDH).

Cells isolated from fat pads of both groups of animals underwent differentiation as shown by the high level of G3PDH specific activity and by the presence of accumulated triglycerides. However, the level of G3PDH specific activity was 60% lower in cells isolated from animals treated with EGF at a dose of 1 µg/g. Calculation of G3PDH specific activity from 5 separate experiments indicated that, in control animals, G3PDH specific activity was 812±107 mU/mg protein. In animals treated with EGF (1 µg/g), G3PDH specific activity was 337±53 mU/mg protein. This difference in G3PDH activity was correlated with lower frequency of differentiation of cells from EGF-treated animals. The number of cells having accumulated triglycerides was higher in cells from control animals compared to EGF-treated animals. In contrast, the frequency of undifferentiated, fibroblast-like cells appeared higher in cultures from EGF-treated animals.

Analysis of all experiments performed show that the differentiation capacity of precursors from EGF-treated fat pads was 30% to 60% lower than controls, depending on dose of EGF. No further increase in G3PDH specific activity or frequency of differentiation was observed when cells from EGF-treated fat pads were maintained in culture for a longer periods (up to 15 days). This indicates that the reduced differentiative capacity induced by EGF was not simply due to a delay in the onset or rate of differentiation in culture. Measurement of other markers of adipocyte differentiation, including triglyceride accumulation and G3PDHmRNA expression and mouse adipocyte binding protein (aP2) mRNA expression, gave essentially identical results.

EXAMPLE IV

EGF Effect on Adipocyte Precursor Differentiation and Proliferation

Studies from the present inventor's laboratory (10) have shown that the differentiation in vitro of adipocyte precursors cultivated in 4F medium was inhibited in a dose-dependent manner by EGF added to the medium. Experiments were thus conducted to test the responsiveness of adipocyte precursors isolated from EGF-treated animals to the differentiation inhibitory activity of EGF in culture.

Figure 4:
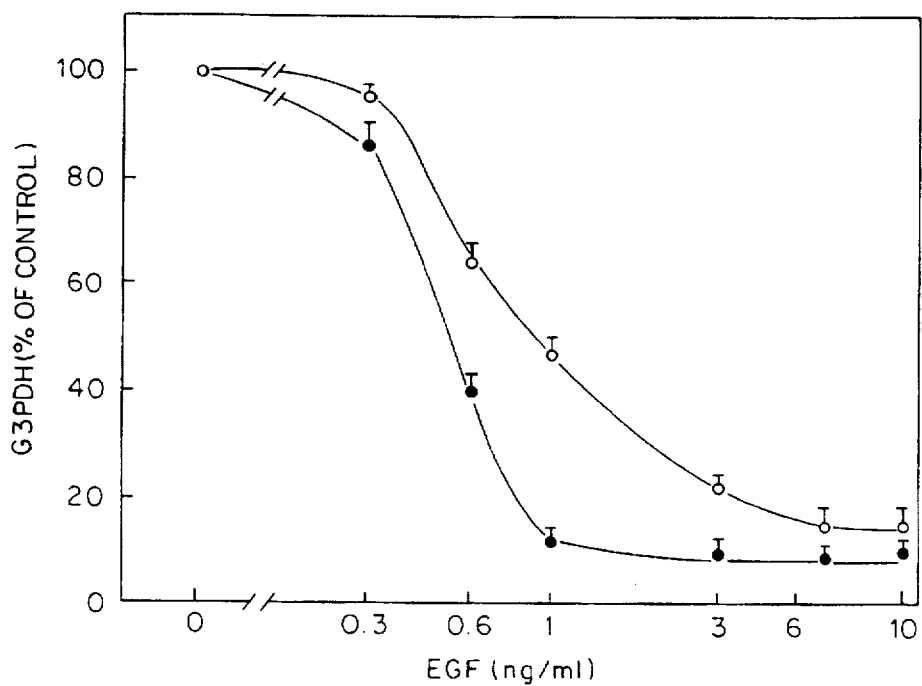
FIG. 4 is a graph showing the effect of EGF treatment on differentiation of adipocyte precursors isolated from inguinal fat pads, measured as specific activity of the enzyme G3PDH. Control rats: open circles; EGF-treated rats: closed circles. In controls, 100% activity corresponds to 812±107 milliunits/mg protein; in EGF-treated rats, 100% corresponds to 337±53 milliunits/mg protein. Values represent means±standard errors.

For this purpose, adipocyte precursors isolated from inguinal fat pads of control or EGF-injected animals (1 µg/g body weight) were cultivated in 4F medium alone or in the presence of increasing concentrations of EGF. The adipocyte precursors from EGF-treated rats displayed in culture an increased sensitivity to the inhibitory action of EGF compared to precursors from control rats, measured as G3PDH enzyme activity (FIG. 4). The $ED_{50}$ for EGF on cells from EGF-treated animals was calculated to be 0.5 ng/ml, compared to an $ED_{50}$ of 0.9 ng/ml for EGF acting on control cells.

Figure 5:
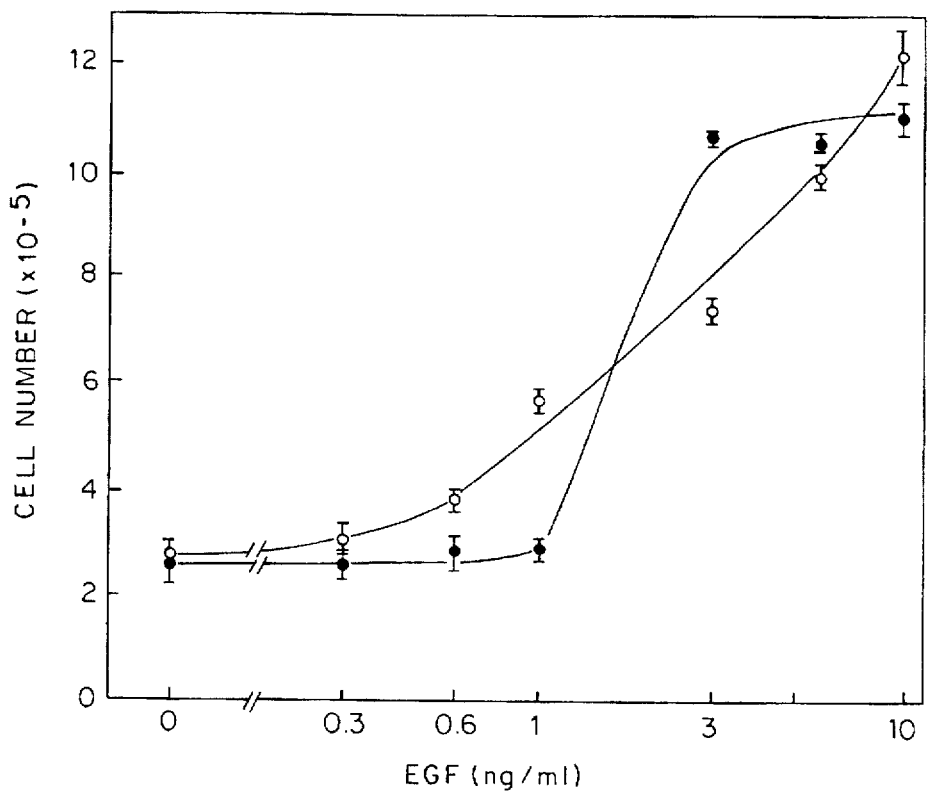
FIG. 5 is a graph showing the effect of EGF on proliferation of adipocyte precursors. Controls and EGF-treated animals as in FIG. 4. After 8 days of culture, cells were detached with trypsin and counted on a Coulter counter. Values represent means±standard errors.

The addition of EGF to the 4F medium stimulated proliferation of adipocyte precursors from both control and EGF-treated rats (FIG. 5), and the difference between groups was less pronounced than the difference in differentiation inhibition. Moreover, when comparing the EGF effect on differentiation and proliferation, the concentration of EGF which inhibited differentiation by 50% had moderate or no effects on cell proliferation. Marked stimulation of proliferation (in cells from controls or EGF-treated rats) was observed only at EGF concentrations above 1 ng/ml.

These findings suggest that the EGF effect on differentiation may not be directly related to its effect on proliferation. The properties of adipocytes from EGF-treated rats, namely, a decreased ability to differentiate and an increased sensitivity to EGF in vitro, could not be explained by occupancy of EGF receptors at the time of cell isolation. Binding studies using $^{125}$I-EGF showed that EGF binding to EGF receptors on adipocytes precursors from control and treated rats (with or without acid wash) was indistinguishable, about 4 pg EGF bound per $10^5$ cells.

One question raised by the above results is whether the inhibition of adipose tissue development by EGF is due to a direct action of EGF on adipose tissue or by indirect action via another growth factor or hormone. Several observations point to direct action of EGF: EGF inhibits the differentiation of primary culture of adipocyte precursors freshly isolated from inguinal fat pads (10); adipocyte precursors have specific EGF receptors on their surface (10). In whole animal experiments, $^{125}$I-EGF injected sc into newborn rats specifically bound to several organs including inguinal fat pads. Skin, a known target of EGF action in vivo (30), also showed a high level of $^{125}$I-EGF binding.

In the above studies, the sc route of administration of EGF was chosen because of small body size and to ensure retention of the full injected volume. The EGF level achieved by daily sc injection of doses between 0.1 to 1 µg/g body weight was not determined. However, it is noteworthy that a significant delay of adipose tissue development was already observed at EGF doses as low as 0.3 µg/g body weight and that the effect of EGF on adipose tissue development was not due to a generalized inhibitory effect on development. These data indicate that adipose tissue is a target for EGF action in vivo.

EXAMPLE V

Effect of Neonatal EGF Treatment on Body Weight

Figure 6:
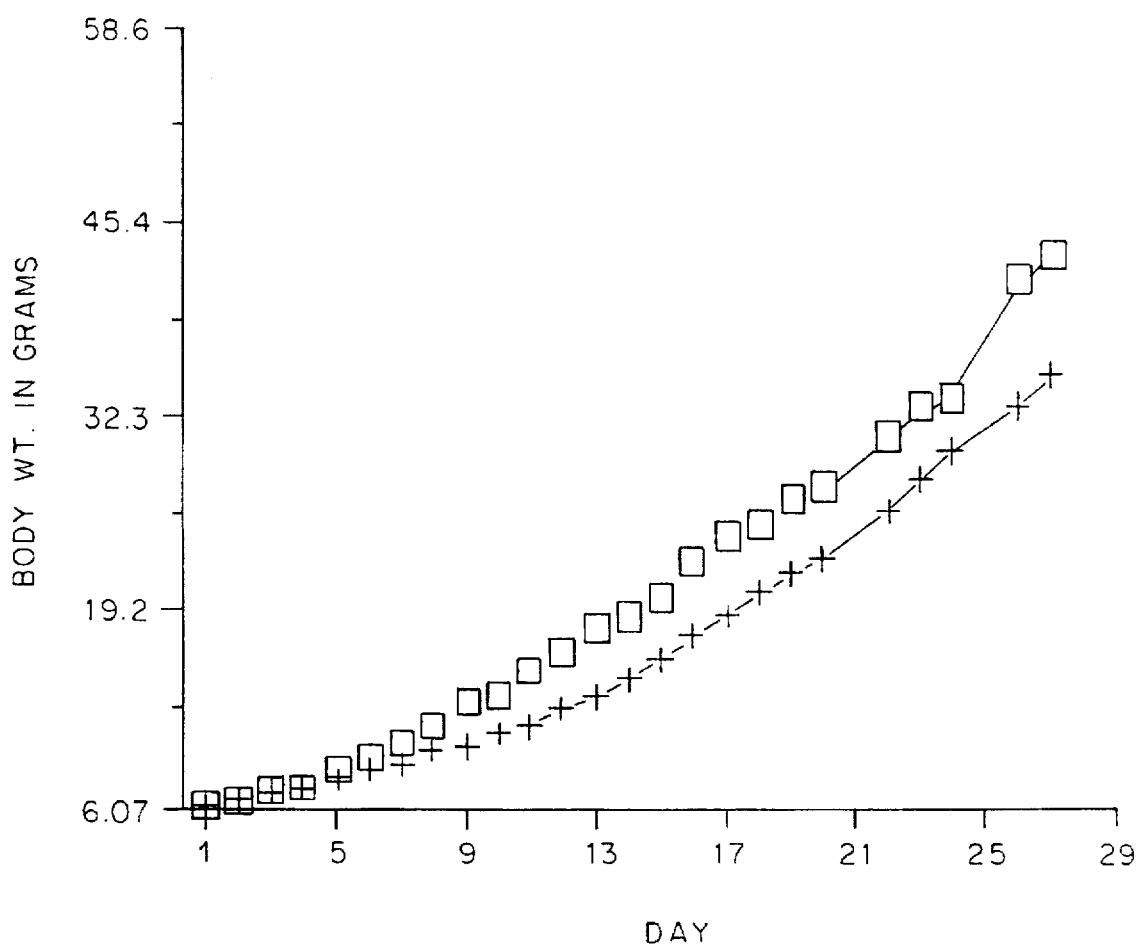
FIG. 6 is a graph showing the effect of EGF treatment of newborn rats on development of body weight over 28 days. Rats were injected beginning at 24 hours after birth with EGF (0.6 μg/g body weight) (filled squares) or with vehicle (PBS) (+) for 9 days.
Figure 7:
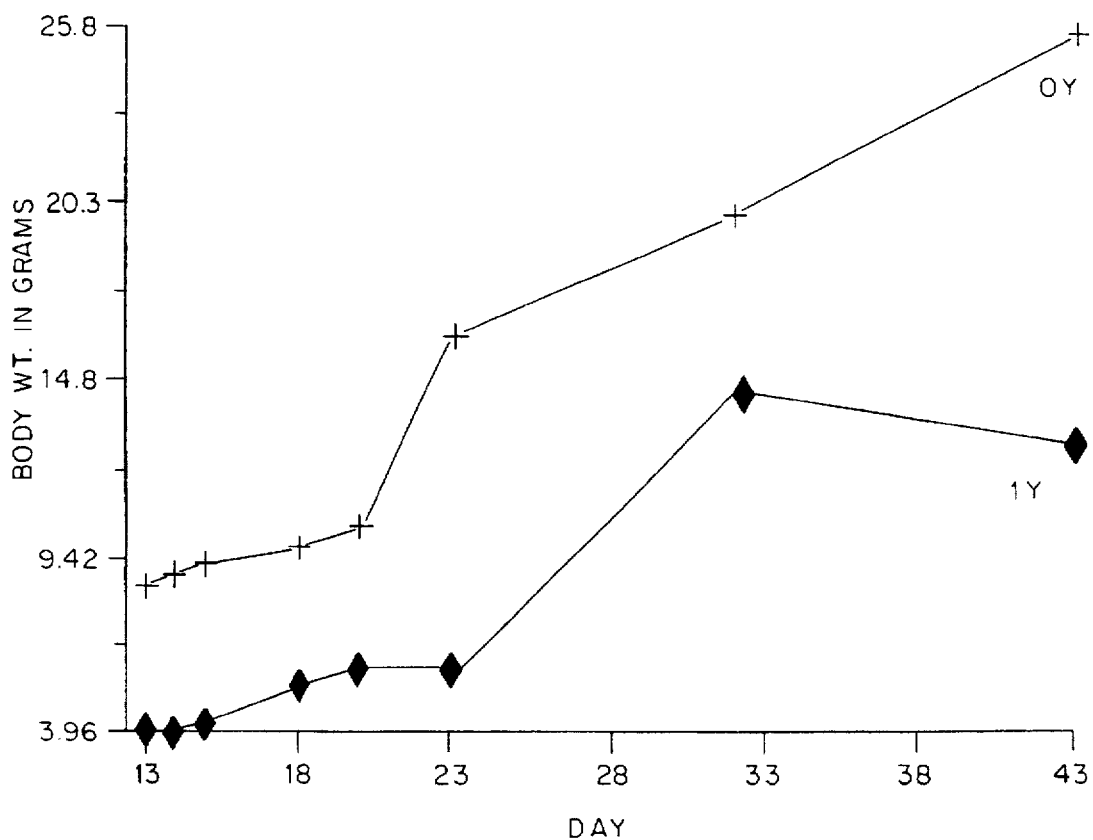
FIG. 7 is a graph showing the effect of EGF treatment on development of body weight in obese yellow mice over 43 days. Mice were injected beginning at 24 hours after birth with EGF (1 μg/g body weight) (filled diamonds, marked 1Y) or with vehicle (PBS) (+, marked OY) for 9 days. Weights are shown beginning at postnatal day 13

Additional experiments indicated that a 9–10 day course of EGF administration in neonatal rats or obese mice had a prolonged effect on body weight. As shown in FIG. 6, rats treated with EGF at a dose of 0.6 μg/g body weight showed a significant reduction in body weight over a 28 day period. Obese yellow mice treated with EGF at a dose of 1 μg/g body weight from day 1 to day 10 of life showed a prolonged and profound diminution in body weight over at least 43 days. These results support the concept that can EGF not only act as a physiological regulator of adipose tissue development in vivo, but can also serve as a therapeutic agent capable of promoting a reduction in obesity.

EXAMPLE VII

EGF Levels are Decreased in Obese Mice

Figure 8:
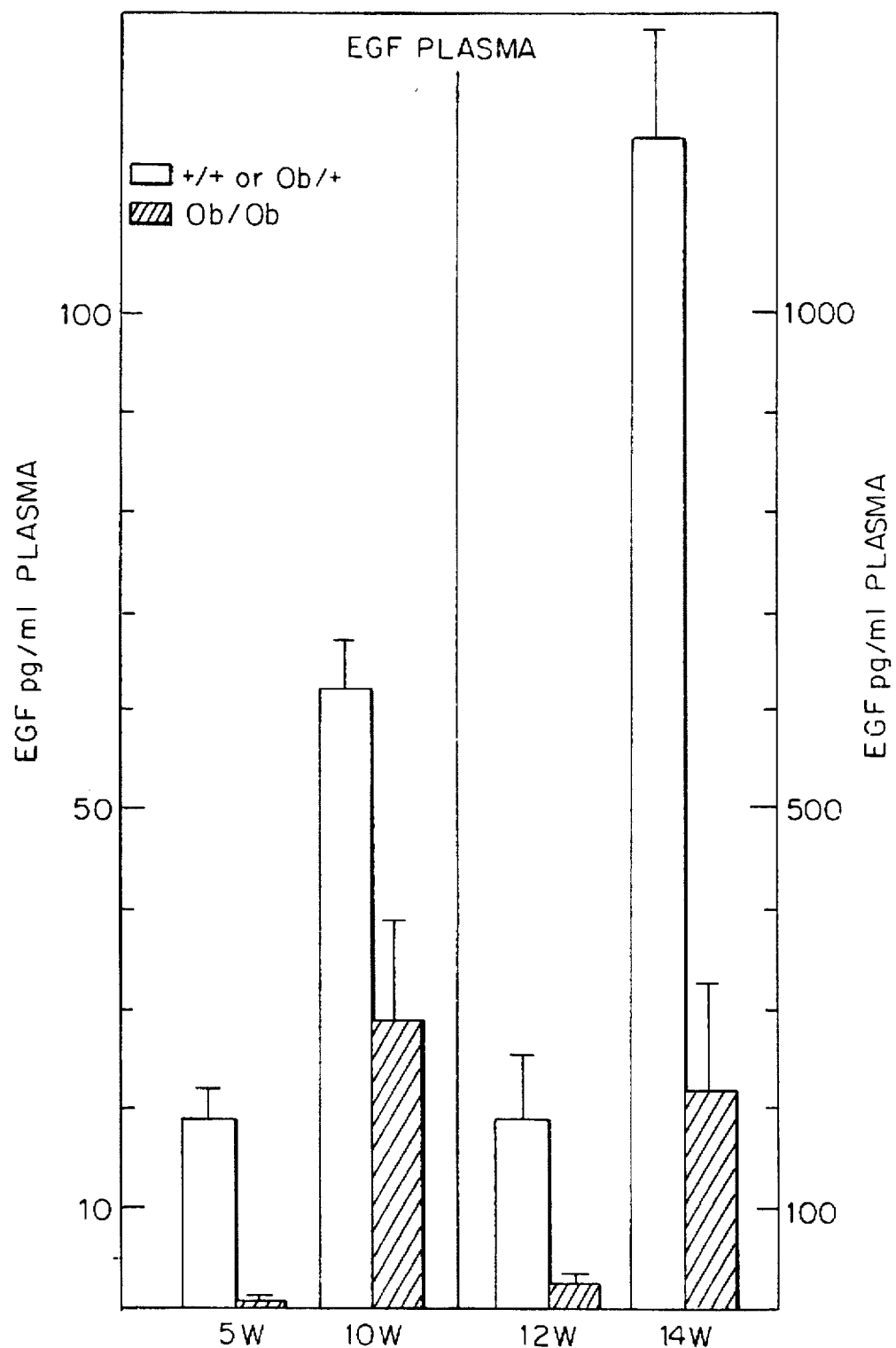
FIG. 8 is a graph showing EGF levels in plasma of normal (open bars) and obese (hatched bars) mice at 5, 10, 12 and 14 weeks (W) of age. Note that two different scales are used for the 5 and 10 week groups compared to the 12 and 14 week groups.
Figure 9:
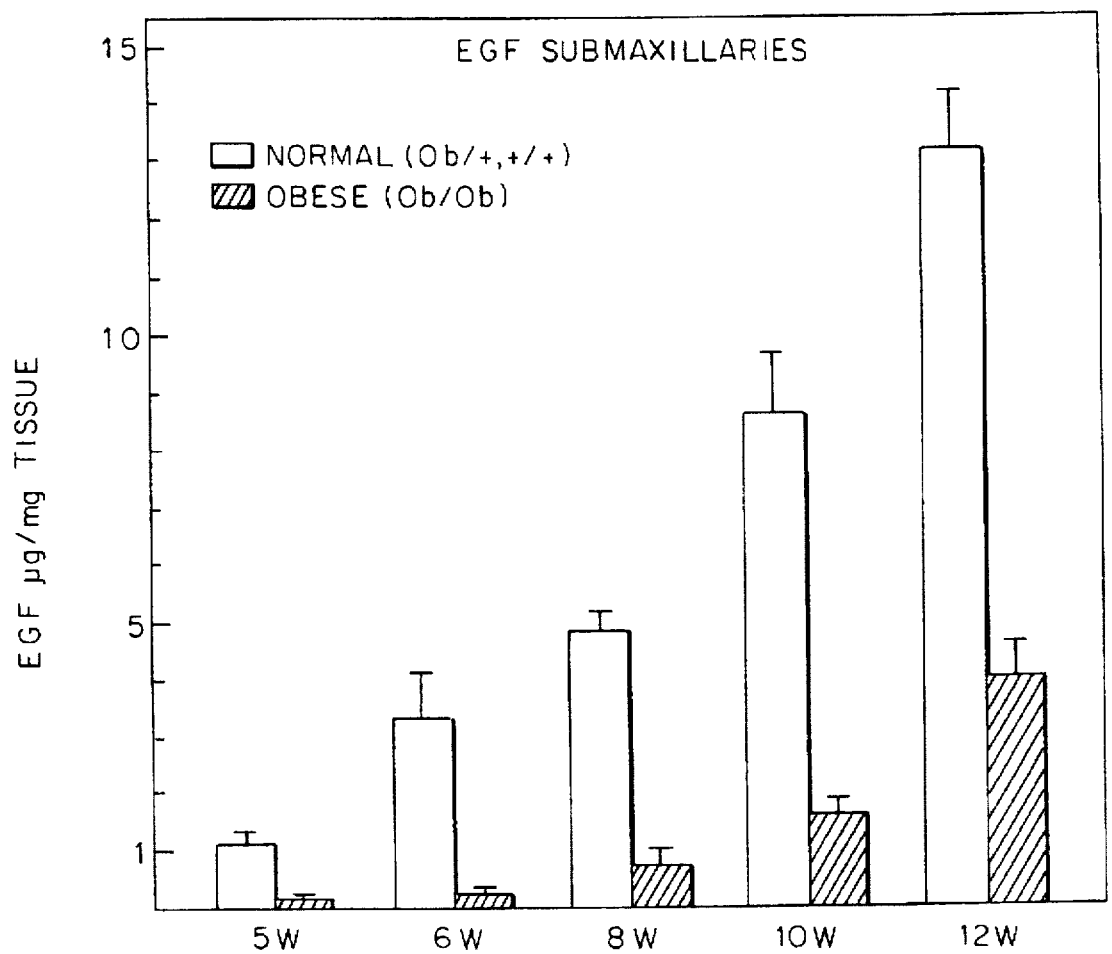
FIG. 9 is a graph showing EGF levels in extracts of submaxillary glands of normal (open bars) and obese (hatched bars) mice at 5, 6, 8, 10 and 12 (W) of age.

EGF concentrations were measured by conventional radioimmunoassay in the plasma and submaxillary gland of genetically obese mice having the Ob/Ob genotype and compared to normal controls (both +/+ homozygotes and Ob/+ heterozygotes). FIG. 8 shows EGF levels in plasma of normal and obese mice aged 5 to 14 weeks. FIG. 9 shows EGF levels in submaxillary gland extracts of normal and obese male mice aged 5–12 weeks. The results indicate that genetically obese mice have an approximately 80–95% decrease in the plasma and submaxillary gland levels of EGF.

It is therefore postulated that EGF plays an important functional role in the regulation of adipose tissue development. Abnormalities in the level of EGF or its receptor account for abnormal adipose tissue development, with an EGF deficiency being strongly associated with obesity. Additional support for this conclusion comes from reports that obese rodents have either reduced levels of EGF (diabetic db/db mice; ref. 31) or EGF receptors (32).

EXAMPLE VIII

Interactions between EGF and the Arachidonic Acid Pathway

Experiments were performed to examine whether stimulation of adipocyte precursors, either primary cultures or the 1246 cell line, activated the enzyme phospholipase A2 (PLA2) which results in the activation of cyclooxygenase and the generation of prostaglandins.

Figure 10B:
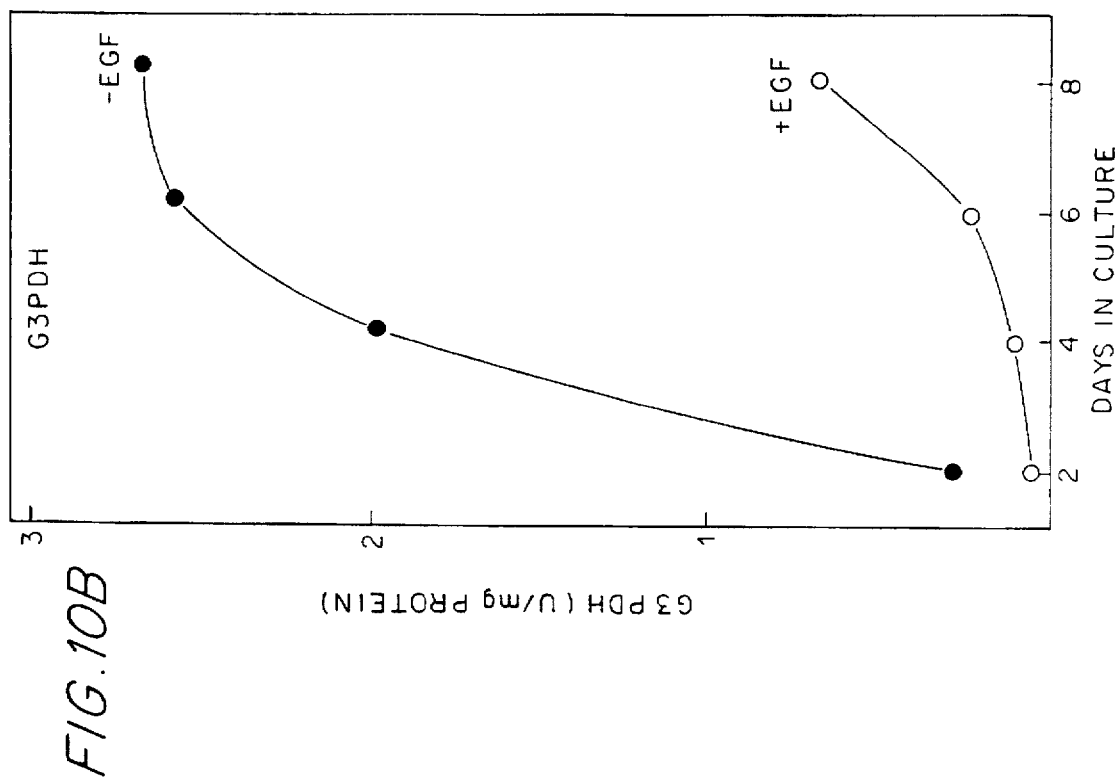
FIG. 10A–10B is graph showing EGF stimulation of phospholipase A2 (PLA2) enzymatic activity in primary cultures of adipocyte precursor cells in vitro (left panel. Also shown is the concomitant inhibition by EGF of differentiation, measured as G3PDH enzymatic activity. EGF was present in cultures at 10 ng/ml.
Figure 10A:
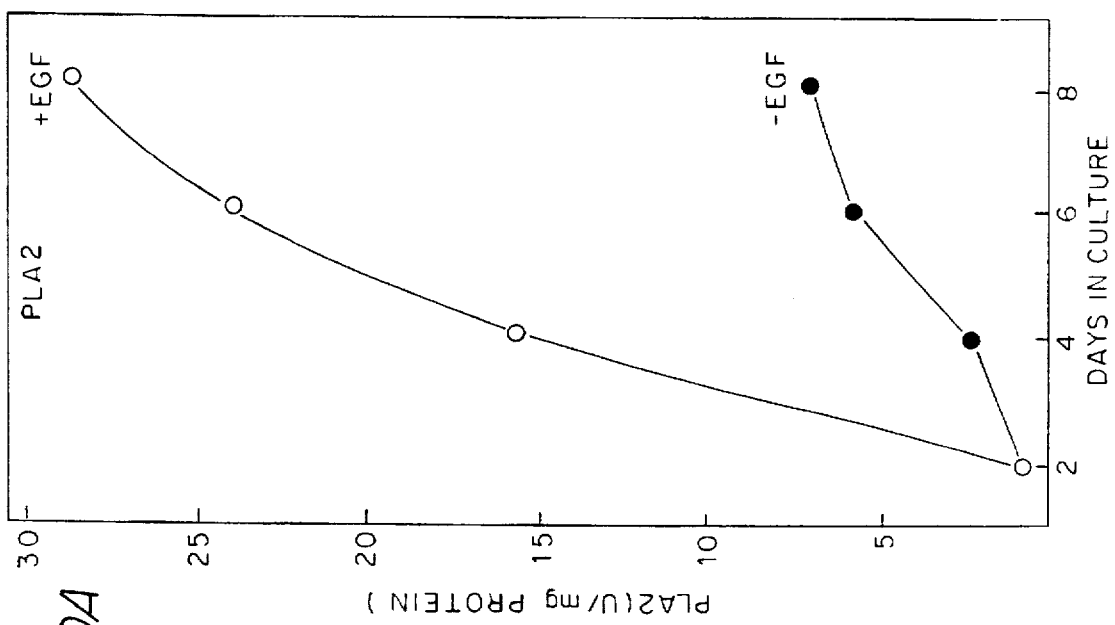

EGF at a concentration of 10 ng/ml was found to stimulate a concomitant increase in PLA2 activity and inhibition of differentiation, as measured by diminished G3PDH activity (FIG. 10A–10B).

Figure 11:
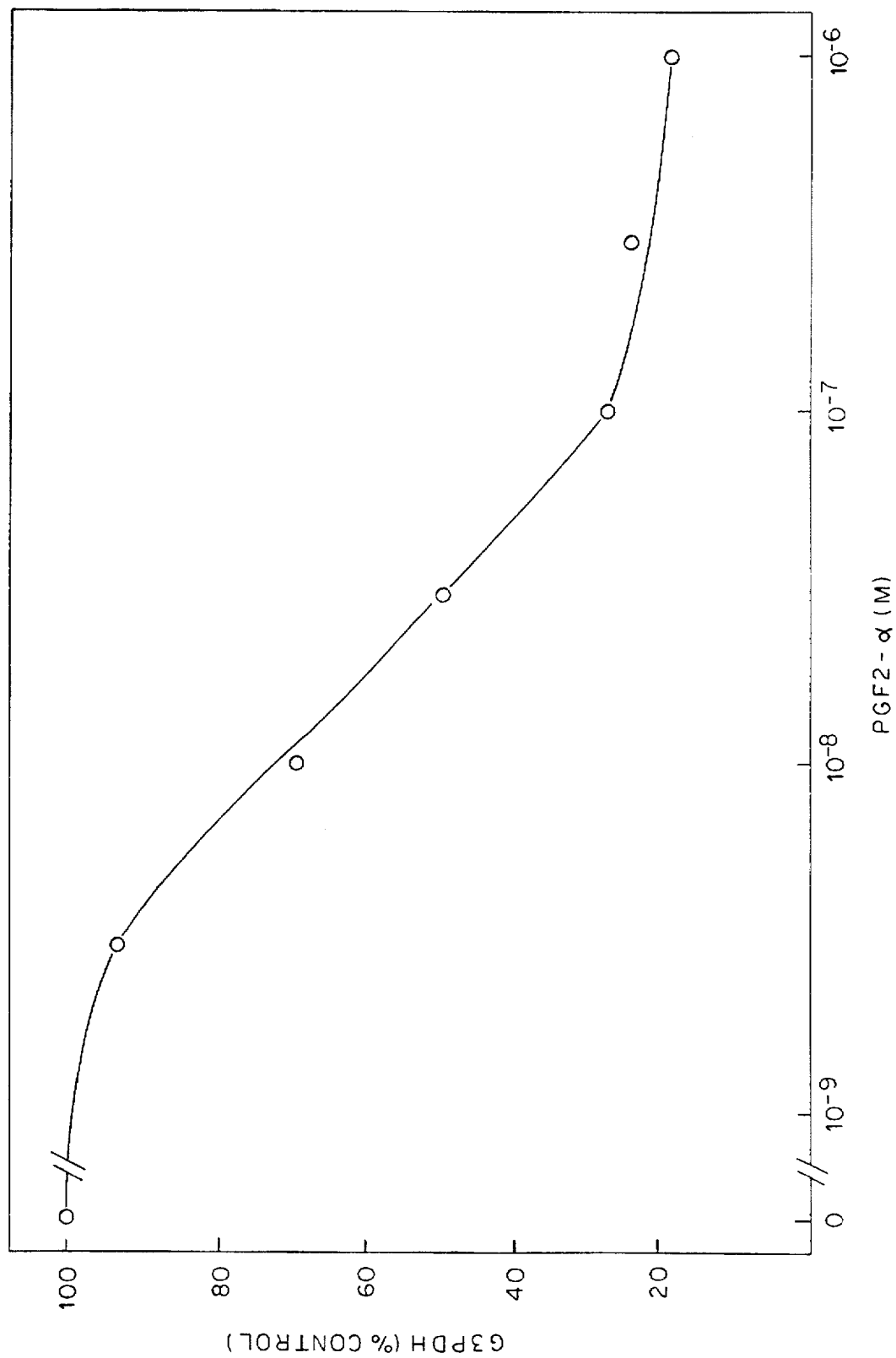
FIG. 11 is a graph showing the dose-related inhibition of adipocyte differentiation by prostaglandin $F_{2\alpha}$ ($PGF^{2\alpha}$). 1246 cells were incubated with the indicated dose of $pGF^{2\alpha}$

Stimulation of PLA2 will result in the activation of the cyclooxygenase pathway, leading to generation of various prostaglandins, as is well-known in the art. One metabolite of this pathway, prostaglandin $F_{2\alpha}$ ($PGF_{2\alpha}$), was tested for its ability to act as a mediator of the EGF effect and inhibit adipocyte differentiation. As is shown in FIG. 11, $PGF_{2\alpha}$ showed a concentration-dependent inhibition of differentiation of 1246 cells.

Figure 12:
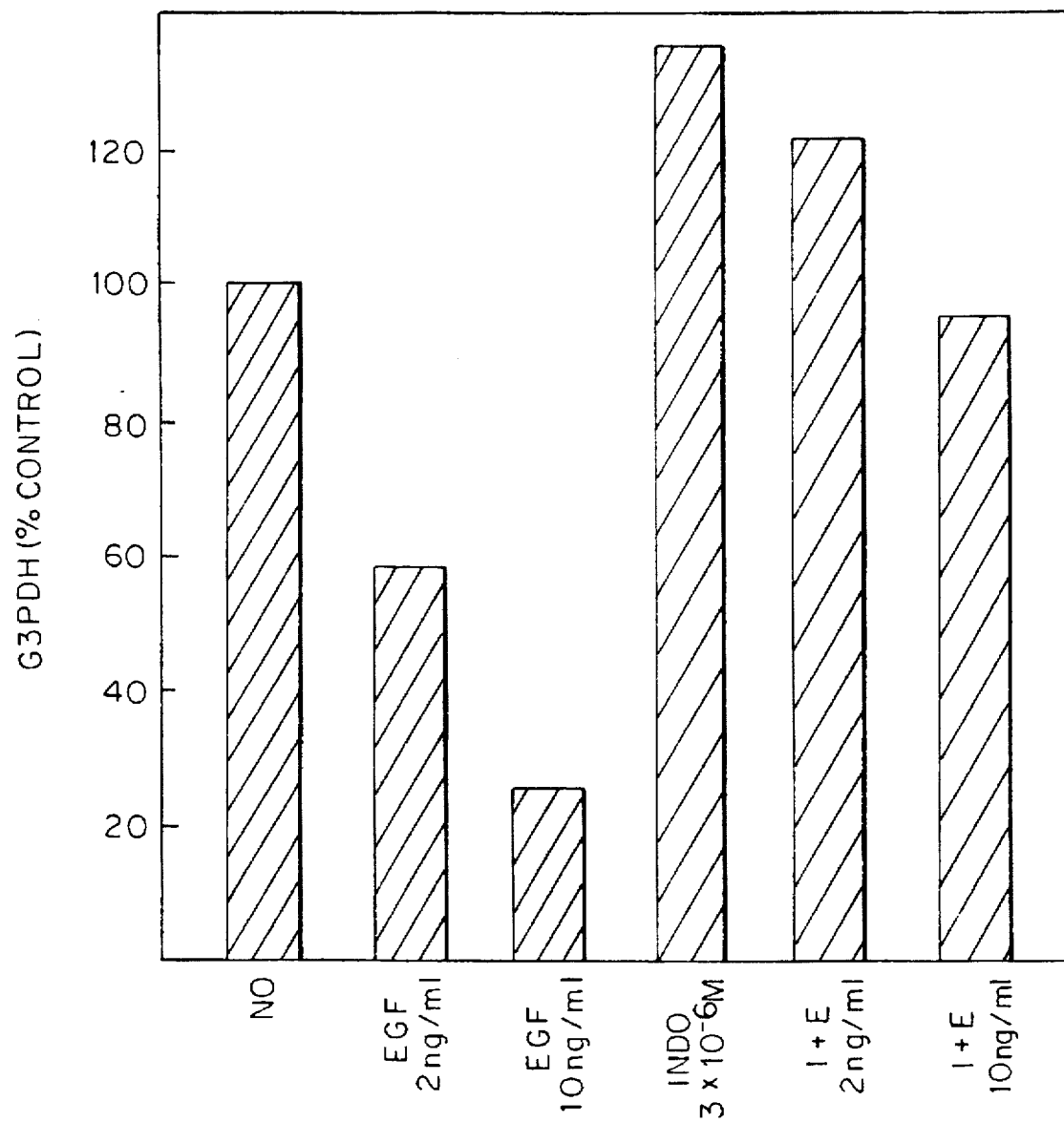
FIG. 12 is a graph showing that indomethacin reverses the EGF-induced inhibition of adipocyte differentiation. 1246 cells were incubated in medium ("no"=control, 100% of activity) or in the presence of indicated concentrations of EGF, indomethacin ("Indo") or a mixture of EGF (E) at the indicated concentration and indomethacin (I) at 3 μM. As above, differentiation was assessed as G3PDH enzymatic activity.

If EGF inhibits adipocyte differentiation via the activation of PLA2 and cyclooxygenase, it would be expected that an inhibitor of cyclooxygenase would counteract the EGF effect. Indeed, upon addition of the cyclooxygenase inhibitor indomethacin (at a concentration of 3 μM) to cultures incubated with EGF (at 2 or 10 ng/ml), it was found that the EGF inhibition of adipocyte differentiation was completely reversed (FIG. 12).

This finding supports the idea that EGF acts on adipocytes at least in part by generating prostaglandins, and points the way to an additional therapeutic approach to those forms of obesity related to EGF-adipocyte precursor interactions.

REFERENCES CITED BY NUMBER

1. Green, H. (1979), In: *Obesity: Towards a Molecular Approach*, Colloques de l'Inserm, ed. Ailhaud, G., pp 15–24.
2. Spiegelman, B. M. Distel, R. J., R. O. H. S., Rosen, B. S., & Satterberg, B. (1988) J. Cell Biol. 107, 829–832.
3. Ailhaud, G. (1982) Mol. Cell Biochem. 49, 17–31.
4. Zezulak, K. M. & Green, M. (1986) Science 233, 551–553.
5. Knight, D. M., Chapman, A. B., Navre, M., Drinkwater, L., Bruno, J. J. & Ringold, G. M. (1987) Mol. Endocrin. 1, 36–43.
6. Hayashi, I., Morikawa, M. & Green, H. (1981) Proc. Natl. Acad. Sci. USA 78, 3969–3972.
7. Serrero, G. (1986), In: *Cellular Endocrinology: Hormonal Control of Embryonic and Cellular Differentiation*, eds. Serrero, G. & Hayashi, J. (Alan R. Liss, Inc.) pp. 191–204.
8. Ignotz, R. & Massague, J. (1985) Proc. Natl. Acad. Sci. USA 82, 8530–8534.
9. Navre, M. & Ringold, G. M. (1989) J. Cell Biol. 109, 1857–1863.
10. Serrero, G. (1987) Biochem. Biophys. Res. Commun. 146, 194–202.
11. Cohen, S. (1962) J. Biol. Chem. 237, 1555–1562.
12. Savage, C. R., Jr. & Cohen, S. (1972) J. Biol. Chem. 247, 7609–7611.
13. Carpenter, G. & S. Cohen (1979) Ann. Rev. Biochem. 48, 193–216.
14. Carpenter, G. (1987) Ann. Rev. Biochem. 56, 881–914.
15. Oka, Y., Ghishan, F. K., Greene, H. L. & Orth, D. W. (1983) Endocrinology 112, 940–944.
16. Okamoto, S. & Oka, T. (1984) Proc. Natl. Acad. Sci. USA 81, 6059–6063.
17. Hoath, S. B. (1986) Pediatric Res. 20, 468–472.
18. Tsutsumi, O., Kubota, Y. & Oka, T. (1987) J. Endocrinol. 113, 193 197.
19. Topham, R. T., Chiego, D. J., Gattone, V. H., Hinton, D. A. & Klein, R. M. (1987) Der. Biol. 124, 532–543.
20. Coleman, S., Silberstein, G. B., & Daniel, C. W. (1988) Dev. Biol. 127, 304–315.
21. Maruo, T., Matsuo, H., Oishi, T., Hayashi, M., Nishino, R., & Mochizuki, M. (1987) J. Clin. Endocrin. Met. 64, 744–750.
22. Tsutsumi, O., Kurachi, H. & Oka, T. (1986) Science 233, 975–977.
23. Bjorntorp, P., Karlsson, M., Pertoft, H., Pettersson, P., Sjostrom, L., & Smith, V. (1978) J. Lipid Res. 19, 316 324.
24. Serrero, G. & Mills, D. K. (1987) In Vitro Cell and Devel. Biol. 23, 63–66.
25. Serrero, G. & Khoo, J. C. (1982) Anal. Biochem. 120, 351 359.
26. Bligh, E. G. & Dyer, W. J. (1959) Can. J. Biochem. Physiol. 37, 911. 917.
27. Marsh, J. B. & Weinstein, D. B. (1966) J. Lipid Res. 7, 574–576.
28. Blosse, P. T. & Fenton, E. L. (1974) Biochim. Biophys. Acta 354, 57–60.
29. Heimberg, M., Weinstein, I., LeQuire, V. S. & Cohen, S. (1965) Life Sci. 4, 1625–1633.
30. Cohen, S. & Elliott, G.A. (1963) J. Invest. Dermatol. 40, 1–5.

31. Kasayama, S., Ohba, Y. & Oka, T. (1989) Proc. Natl. Acad. Sci. USA 86, 7644–7648.

32. Blackshear, P. J., Stumpo, D. J., Kennington, E. A., Tuttle, J. S., Orth, D., Thompson, K. L., Hung, M. C. & Rosner, M. R. (1987) J. Biol. Chem. 262, 12356–12364.

All the references cited in the specification above are incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for suppressing precursor adipocyte differentiation in obese mammals, comprising administering to said mammal an effective amount of a composition comprising epidermal growth factor or an epidermal growth factor receptor agonist which binds to the epidermal growth factor receptor and activates said receptor.

2. A method according to claim 1 wherein said composition is epidermal growth factor.

3. A method according to claim 1 wherein said epidermal growth factor receptor agonist is an antibody specific for the epidermal growth factor receptor.

4. A method according to claim 1 wherein said epidermal growth factor receptor agonist is an anti-idiotypic antibody specific for an idiotope on an antibody specific for epidermal growth factor.

5. A method in accordance with claim 1, wherein said step of administering said composition is in conjunction with the step of treating said mammal with an anti-obesity therapy which causes removal of adipocyte cells.

6. A method in accordance with claim 5, wherein said anti-obesity therapy is liposuction or lipectomy.

7. A method for suppressing precursor adipocyte differentiation in an obese patient who has been treated with an anti-obesity therapy which causes removal of adipocyte cells, comprising administering to said patient an effective amount of a composition comprising epidermal growth factor or an epidermal growth factor receptor agonist capable of binding the epidermal growth factor receptor and activating said receptor.

8. A method in accordance with claim 7, wherein said anti-obesity therapy is liposuction or lipectomy.

9. A method in accordance with claim 7, wherein said composition comprises epidermal growth factor.

10. A method in accordance with claim 7, wherein said epidermal growth factor receptor agonist is an antibody specific for the epidermal growth factor receptor.

11. A method in accordance with claim 7, wherein said epidermal growth factor receptor is an anti-idiotypic antibody specific for an idiotope on an antibody specific for epidermal growth factor.

* * * * *